(12) United States Patent  
Pinyayev et al.

(10) Patent No.: US 12,331,267 B2  
(45) Date of Patent: Jun. 17, 2025

(54) METHODS FOR MAKING UNIT DOSE ARTICLES

(71) Applicant: The Procter & Gamble Company, Cincinnati, OH (US)

(72) Inventors: Aleksey Mikhailovich Pinyayev, Cincinnati, OH (US); Travis Kyle Hodgdon, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 750 days.

(21) Appl. No.: 16/271,923

(22) Filed: Feb. 11, 2019

(65) Prior Publication Data

US 2019/0256809 A1 Aug. 22, 2019

Related U.S. Application Data

(60) Provisional application No. 62/633,623, filed on Feb. 22, 2018.

(51) Int. Cl.

| | |
|---|---|
| *B29C 64/118* | (2017.01) |
| *A61K 8/11* | (2006.01) |
| *A61K 9/48* | (2006.01) |
| *B33Y 10/00* | (2015.01) |
| *B33Y 70/10* | (2020.01) |
| *B33Y 80/00* | (2015.01) |
| *C11D 1/62* | (2006.01) |
| *C11D 3/00* | (2006.01) |
| *C11D 3/12* | (2006.01) |
| *C11D 3/20* | (2006.01) |
| *C11D 3/37* | (2006.01) |
| *C11D 3/50* | (2006.01) |
| *C11D 17/00* | (2006.01) |
| *C11D 17/04* | (2006.01) |
| *D04H 3/02* | (2006.01) |
| *D04H 3/14* | (2012.01) |
| *B29K 105/00* | (2006.01) |

(52) U.S. Cl.
CPC ............. *C11D 17/042* (2013.01); *A61K 8/11* (2013.01); *A61K 9/48* (2013.01); *B29C 64/118* (2017.08); *B33Y 80/00* (2014.12); *C11D 1/62* (2013.01); *C11D 3/001* (2013.01); *C11D 3/1253* (2013.01); *C11D 3/2075* (2013.01); *C11D 3/373* (2013.01); *C11D 3/505* (2013.01); *C11D 17/00* (2013.01); *D04H 3/02* (2013.01); *D04H 3/14* (2013.01); *B29K 2105/0029* (2013.01); *B33Y 10/00* (2014.12); *B33Y 70/10* (2020.01); *C11D 2111/12* (2024.01)

(58) Field of Classification Search
CPC .................................................. C11D 17/042
See application file for complete search history.

(56) References Cited

U.S. PATENT DOCUMENTS

| | | | |
|---|---|---|---|
| 2,975,099 A | 3/1961 | Goyan | |
| 4,396,522 A | 8/1983 | Callicott | |
| 4,899,398 A | 2/1990 | Hutchings | |
| 5,004,601 A | 4/1991 | Snipes | |
| 5,367,003 A | 11/1994 | Petcavich | |
| 5,503,785 A | 4/1996 | Crump | |
| 5,709,940 A | 1/1998 | George | |
| 6,070,107 A | 5/2000 | Lombardi | |
| 6,228,923 B1 | 5/2001 | Lombardi | |
| 6,437,034 B2 | 8/2002 | Lombardi | |
| 6,488,963 B1 | 12/2002 | Mcginity | |
| 6,790,403 B1 | 9/2004 | Priedeman, Jr. | |
| 6,822,135 B2 | 11/2004 | Soerens et al. | |
| 7,754,807 B2 | 7/2010 | Priedeman, Jr. | |
| 8,246,888 B2 | 8/2012 | Hopkins | |
| 8,822,590 B2 | 9/2014 | Hermes | |
| 10,259,921 B2 | 4/2019 | Bayer | |
| 10,717,839 B2 | 7/2020 | Mao et al. | |
| 2004/0260034 A1 | 12/2004 | Haile | |
| 2009/0220579 A1* | 9/2009 | Hassingboe | D01D 5/14 428/375 |
| 2011/0060445 A1 | 3/2011 | Heenan | |
| 2012/0021026 A1* | 1/2012 | Glenn, Jr. | D04H 1/728 424/59 |
| 2012/0048769 A1* | 3/2012 | Sivik | B29C 43/22 206/524.1 |
| 2012/0213976 A1 | 8/2012 | Xu | |
| 2012/0270765 A1 | 10/2012 | Aouad | |
| 2013/0251798 A1 | 9/2013 | Mckenna | |
| 2015/0007400 A1 | 1/2015 | Gonzales | |
| 2015/0290280 A1 | 10/2015 | Petrak | |
| 2016/0101204 A1 | 4/2016 | Lynch et al. | |
| 2016/0167334 A1* | 6/2016 | Arora | A61F 13/5116 428/137 |
| 2016/0177078 A1 | 6/2016 | Naito | |
| 2016/0194492 A1 | 7/2016 | Smith, Jr. | |
| 2016/0258083 A1 | 9/2016 | Weisman et al. | |
| 2016/0333164 A1 | 11/2016 | Burmeister | |
| 2016/0346997 A1 | 12/2016 | Lewis | |
| 2019/0217536 A1* | 7/2019 | Honorato Ruiz | B33Y 30/00 |

(Continued)

FOREIGN PATENT DOCUMENTS

| | | |
|---|---|---|
| CA | 1246448 A | 12/1988 |
| WO | WO2012003316 A1 | 1/2012 |

(Continued)

OTHER PUBLICATIONS

Gibson et al., "Rapidpre: A new additive manufacturing technique based on reaction injection moulding", Annals of DAAAM for 2010 & Proceedings of the 21st International Symposium, vol. 21, No. 1, ISSN 1726-9679, 2 pgs.

(Continued)

*Primary Examiner* — Farah Taufiq

(74) *Attorney, Agent, or Firm* — Kathleen Y. Carter; Sarah M. DeCristofaro; Matthew J. Spegele

(57) ABSTRACT

A method for forming an object includes steps of forming a non-woven mat from one or more strands of meltable material and subsequently forming discrete units from the non-woven mat where portions of the surface of the formed discrete units are locally densified.

13 Claims, No Drawings

(56) References Cited

FOREIGN PATENT DOCUMENTS

| WO | WO2016020435 A1 | 2/2016 |
| WO | WO2016020442 A1 | 2/2016 |
| WO | WO2016020447 A1 | 2/2016 |
| WO | WO2016020454 A1 | 2/2016 |
| WO | WO2016172699 A1 | 10/2016 |
| WO | WO2017106191 A1 | 6/2017 |
| WO | WO2018213170 A1 | 11/2018 |

OTHER PUBLICATIONS

W.M. Keck Center for 3D Printing at University of Texas El Paso website, http://keck.utep.edu/.

International Search Report and Written Opinion dated May 2, 2019, U.S. Appl. No. 16/271,923, 13 pgs.

\* cited by examiner

METHODS FOR MAKING UNIT DOSE ARTICLES

FIELD OF THE INVENTION

The invention relates to method for manufacturing discrete articles. The invention relates particularly to methods for manufacturing unit dose consumer product articles.

BACKGROUND OF THE INVENTION

Single use, or unit dose consumer goods are known in the art. Single use articles such as laundry pods, automatic dishwasher pods, fabrics softener sheets for clothes dryer use are each well known as are discrete single serving food items. Varying methods for the manufacture of such articles are known and are intimately related to the structures of the articles themselves. Unit does articles comprising a film or web may be manufactured using web handling methods. Pods, active chemistries enclosed in a soluble film, may be formed by forming a film cavity, filling the cavity and sealing the cavity with additional film portions. Some unit dose items may comprise a filled rigid shell wherein the filling differs from the shell and the formation may be accomplished by various known means. A unit dose having a substantially homogeneous composition but benefitting from a shell and core structure may enable unique consumer benefits. What is needed is a method for manufacturing discreet articles having such a homogeneous composition together with a shell and core structure.

SUMMARY OF THE INVENTION

In one embodiment, a method for forming an object includes steps of forming a non-woven mat from one or more strands of meltable material and subsequently forming discrete units from the non-woven mat where portions of the surface of the formed discrete units are locally densified.

DETAILED DESCRIPTION OF THE INVENTION

As used herein, the term: "locally densified" means that the referenced portion or element has a greater density than at least some of the material adjacent to the referenced portion despite other similarities between the materials. A measure of material density taken to include the referenced portion and adjacent portions would demonstrate a density gradient with the referenced portion having a greater density.

As used herein, the term: "meltable" means a material having a phase transition temperature such that at or near the phase transition temperature the material transitions from a solid to a semi-solid and then to a liquid as the energy input to the material continues and the temperature rises, and the material becomes subject to deformation and flow when acted upon, while below the phase transition temperature the material is solid and in a glassy, crystalline or semi-crystalline state and not subject to deformation and flow when acted upon.

In one embodiment, a method for forming an object comprises the steps of: providing semi-solid stands of a meltable material, forming a non-woven mat comprising the strands of meltable material; and forming discrete units of the non-woven mat, wherein the surface of the discrete units comprises a locally densified portion.

As used herein, the terms: "strand" and "strands" are used interchangeably to refer to the individual materials used in the fabrication of the described articles. The articles may be formed from the proper manipulation of a single strand of material or from a plurality of strands of the material. The use of either strand or strands in any particular portion of the description should not be read as limiting that portion of the description or the invention regarding the number of strands utilized.

The meltable material may comprise a wax, thermoplastic starch or hydrocarbon based thermoplastic materials and polymers. The strand material may be water soluble. The material may be heated beyond the phase transition temperature of the material and drawn or otherwise extruded into one or more strands of the material. The strands of the material may be maintained at or above the phase transition temperature or cooled and subsequently reheated to a temperature at or above the phase transition temperature to render the strand(s) to a semi-solid state. In one embodiment, the strands comprise a filament having a diameter of between about 0.3 and about 2 millimeters. In one embodiment, the strands comprise a filament having a diameter of between about 0.4 and about 1.5 millimeters. In one embodiment, the strands comprise a filament having a diameter of between about 0.5 and about 1 millimeters. In another embodiment, the strands comprise a filament having a diameter of between about 1 and about 2 millimeters.

Exemplary meltable materials include: metals, hydrocarbon based thermoplastic resins such as: polyethylene, polypropylene, polyethylene glycol, waxes, surfactants, fatty acids, fatty alcohols, fatty esters, fats, foods (chocolate).

Waxes can include compounds containing hydrogen, oxygen and carbon and may be derived from animal, plant, or petroleum sources. In one embodiment, the wax may include from about 15 to about 50 carbon atoms. They may be linear, branched, saturated, unsaturated, cyclic and combinations thereof. Waxes may contain one or more functional groups such as hydroxyl, carboxylate, carboxyl, ester, ethoxy, ether, acetal, aldehyde, ethoxy and ketones. Examples of waxes include beeswax, Chinese, lanolin, shellac, spermaceti, bayberry, candelilla, carnauba, castor, esparto, Japan, ouricury, rice bran, soy, tallow tree, ceresin, montan, ozocerite, peat, montan, paraffin, microcrystalline, myristic acid, stearic acid, isostearic acid, cetearic acid, dodecanoic acid, linoleic acid, oleic acid, palmitic acid, lauric acid, cetyl alcohol, stearyl alcohol, behenyl alcohol, lauryl alcohol, myristic alcohol, isostearyl alcohol, arachidyl alcohol and ethoxylated fatty alcohols. In one embodiment, a mixture of waxes can be used.

Meltable materials include molecules or mixtures of molecules containing from about 15 to about 50 carbon atoms, hydrogen and at least one heteroatom other than oxygen. The hydrocarbon chains may be linear, branched, saturated, unsaturated, cyclic and mixtures thereof. Examples of meltable molecules may include single, double or tri-tailed surfactants, gemini surfactants, zwitterionic surfactants, anionic surfactants, cationic surfactants and ethoxylated ionic surfactants. Preferred cationic surfactants include di(tallowyloxyethyl)hydroxyethylmethylammoniummethylsulfate, dimethyl bis(stearoyl oxyethyl)ammonium chloride, dimethyl bis(tallowyloxyethyl)ammonium chloride, dimethyl bis(tallowyloxyisopropyl)ammonium methylsulfate. In one embodiment, a mixture of meltable materials can be used.

Exemplary thermoplastic polymers include: polyvinyl alcohol, polyvinyl alcohol copolymers such as butenediol vinylalcohol copolymers available as Nichigo G-Polymer® from Nippon Gohsei and poly[(vinyl alcohol)-co-poly(ethylene glycol)] available as Kollicoat® from BASF, polyethylene oxide, polyethylene glycol, polyethylene glycol copolymers such as poly[polyethylene glycol-co-polypropylene glycol-co-polyethylene glycol] and poly[polypropylene glycol-co-polyethylene glycol-co-polypropylene glycol available as Pluronics® from BASF, poly(2-oxazoline) and poly (2-ethyl-2-oxazoline) available as Aquazol® from Polymer Chemistry Innovations. In one aspect, the weight average molecular weight of the polymers is greater than 5,000 g/mol or from about 8,000 g/mol to about 5,000,000 g/mol or from about 10,000 g/mol to about 1,000,000 g/mol. In one embodiment, a mixture of thermoplastic polymers can be used.

In one embodiment, the semi-solid strands may comprise a mixture of two or more waxes, thermoplastic starches, hydrocarbon based thermoplastic materials and thermoplastic polymers.

In one embodiment, the semi-solid strands may comprise a mixture of the meltable material and particles or filler material. The particles, or filler material, may comprise materials which are not meltable at the phase transition temperature of the meltable material.

Particles and fillers may be organic, inorganic or of mixed inorganic/organic nature. Suitable particles may be selected from the group consisting of: starches, gums, polysaccharides, proteins, amino acids, water soluble polymers, water degradable polymers, water insoluble polymers, sugars, sugar alcohols, inorganic particles, organic salts, surfactants, fatty amphiphiles and mixtures thereof.

Starches may be sourced from corn, wheat, potato, rice, cassava and tapioca. Starches may be unmodified, modified, or partially degraded. Modified starch may include cationic starch, hydroxyehtyl starch, carboxymethylated starch, and polylactic acid graft-starch and polycaprylactone graft starch. Degraded starches may include dextrin and maltodextrin preferably with a dextrose equivalent of 30 or lower.

Gums can be extracted from natural sources, modified from natural sources or fermented. Suitable natural sources from gums include trees, plants, animals and seeds. Examples of natural gums include gum acacia, gum tragacanth, gum karaya, gum ghatti, nanocrylstalline cellulose, pectin, carrageenan, agar, furcellaran, konjac gum, gelatin, guar gum, locast bean gum, tara gum, cassia gum, mesquite gum, tamarind seed gum, quince seed gum, flaxseed gum, phyllium seed gum, oat gum, and microfibrillated cellulose. Gums may also be modified to create alkali cellulose, salts of carboxymethylcellulose, methylcellulose, hydroxypropyl methylcellulose, hydroxypropyl cellulose and hydroxyethyl cellulose. Examples of fermented gums are xanthan gum, dextran and pullulan.

Suitable water-soluble polymers may be synthesized using vinyl addition reaction or ring opening synthesis. Examples of vinyl addition polymers are polyvinyl alcohol, poly(acrylic acid), poly(methacrylic acid), Poly(2-dimethylamino ethyl methacrylate) methyl chloride quaternary salt, Poly(2-dimethylamino ethylacrylate) methyl chloride quaternary salt, poly(allylamine), polyacrylamide, polymethacrylamide, poly[n-(2-hydroxypropyl) methacrylamide], Poly((3-acrylamidopropyl)trimethylammonium chloride), poly(n-(2-aminoethyl) methacrylamide hydrochloride quantized salt), poly(N-isopropylacrylamide), polyvinylpyrrolidone, poly(diallyl dimethyl ammonium chloride), poly(styrenesulfonic acid), and poly(vinyl phosphoric acid). Examples of ring opening synthesized polymers include poly(2-oxazoline), poly(2-ethyl-2-oxazoline), polyethyleneimine, poly(maleic anhydride), and polyaspartic acid. Water soluble copolymers such as poly(vinyl alcohol)-co-poly (ethylene glycol) available as Kollicoat® from BASF.

Water degradable polymers typically contain an ester bond in their backbone leading to hydrolysis in water. Examples of water degradable polymers include polylactic acid, polyglycolic acid, polybutylene succinate, polycaprolactone, polybutyrate, and poly(glycolic acid-co-lactic acid).

Examples of water insoluble polymers include nylon, polystyrene, polyurethane, polyvinyl chloride, polytetrafluoroethylene, latex and polyethylene. Latex may be natural rubber or synthetic. Commonly available synthetic latexes include nitrile rubber, polychloroprene, butyl rubber, fluorocarbon rubber, polyurethane, styrene-butadiene rubber and blends thereof. Polyethylene particles are available under the tradename VELUSTROL from HOECHST Aktiengesellschaft of Frankfurt am Main, Germany.

Examples of sugars and sugar alcohols include glucose, fructose, galactose, sucrose, maltose, lactose and trehalose. Examples of sugar alcohols include erythritol, threitol, arabitol, ribitol, xylitol, mannitol, sorbitol, galactitol, iditol, volemitol, fucitol, inositol, maltitol and lactitol.

Examples of inorganic particles include silica, fumed silica, precipitated silica, talcum powder, graphite, aluminum oxide, iron oxide, antimony trioxide, copper, bentonite clay, laponite clay, aluminum silicate clay, calcium carbonate, sodium chloride, magnesium chloride, calcium chloride, tetramethyl ammonium chloride, alumina, titanium dioxide, chalk, titanium hydroxide, gypsum powder and sodium sulfate.

Examples of organic salts include choline chloride, betaine, sorbic acid, and uric acid.

Examples of surfactants can be cationic, anionic, nonionic or zwitterinoic and include sodium dodecyl sulfate, sodium dodecylbenzenesulfonate, glucose amide, cetyl and trimethylammonium bromide.

Examples of fatty amphiphiles are fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono-, di- and tri-glycerides, polyglycerine fatty esters, alkyl glyceryl ethers, propylene glycol fatty acid esters, cholesterol, ceramides, fatty silicone waxes, fatty glucose amides, and phospholipids.

Mixtures of fillers may be used. These mixtures can be physical blends of two or more types of fillers or two or more fillers that are melted or dissolved together to form a single filler comprising two or more materials. Suitable methods for forming filler particles include any typical method for creating powders such as grinding, milling, spray drying, roll drying, and prilling.

Every dimension of the filler particles should be smaller than the semi-strand diameter, more preferably less than 0.5 times and more preferably less than 0.1 times the semi-strand diameter. The D50 particle size can be determined by the method below. The D50 of particles may be from between about 0.1 microns and about 200 microns, alternatively from between about 0.2 microns and about 150 microns, alternatively from between about 0.5 microns and about 100 microns. The size of particles can be modified by any common method for segregating or reducing particle size including sieving, grinding, cryogenic grinding, and milling. In one embodiment, the particles are spherical or ellipsoidal in shape. Exemplary filler particles are spherical in shape.

The melting temperature of the particle must be greater than the melting, processing and printing temperatures of the semi-strand. Melting temperature of the particles may be determined through standard methods including differential scanning calorimetry or a melt point apparatus.

In one embodiment, the semi-solid strand may further comprise a plasticizing agent. Plasticizing agents are small molecules that are soluble in the semi-solid strand that reduce melt viscosity. Non-limiting examples of plasticizers include water, polyethylene glycol with a weight average molecular weight of 1,000 g/mol or less, methanol, ethanol, propanol, butanol, ethylene glycol, propylene glycol, diethylene glycol and glycerin.

In one embodiment, the semi-solid strand may further comprise a benefit agent. The benefit agent may comprise: perfumes, pro-perfumes, builders, heavy metal ion sequestrants, surfactants, fabric softeners, antistatic agents, silicones (e.g., silicone oils, cationic silicones, silicone gums, high refractive silicones, and silicone resins), colorants, pigments, aversive agents such as bittering agents, enzymes, coenzymes, enzyme stabilizers, plant derivatives, plant extracts, botanicals, botanical extracts, anti-dandruff agents, antifoaming agents, oral care actives, personal health care actives, vitamins, anti-bacterial agents, anti-microbial agents, antifungal agents, their derivatives, and mixtures thereof. The benefit agent may comprise from between about 0.1 and about 50 weight percent, or from between about 0.2 and about 30 weight percent or from between about 0.5 and about 10 weight percent of the semi-solid strand.

In one embodiment, the benefit agent is at least partially surrounded with a wall material to create a microcapsule. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea cross-linked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, one or more types of microcapsules, for example two microcapsules types having different benefit agents may be used.

In one embodiment, the benefit agent is a perfume oil and may include materials selected from the group consisting of 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and □-dihydro ionone, linalool, ethyllinalool, tetrahydrolinalool, and dihydromyrcenol. Suitable perfume materials can be obtained from Givaudan Corp. of Mount Olive, New Jersey, USA, International Flavors & Fragrances Corp. of South Brunswick, New Jersey, USA, or Quest Corp. of Naarden, Netherlands. In one aspect, the benefit agent is a perfume microcapsule.

In one embodiment, the benefit agent is encapsulated in a shell. In one embodiment, the encapsulated benefit agent is perfume oil and the shell is a polymer.

In one embodiment, the benefit agent is a silicone. Useful silicones can be any silicone comprising compound. In one embodiment, the silicone polymer is selected from the group consisting of cyclic silicones, polydimethylsiloxanes, aminosilicones, cationic silicones, silicone polyethers, silicone resins, silicone urethanes, and mixtures thereof. In one embodiment, the silicone is a polydialkylsilicone, alternatively a polydimethyl silicone (polydimethyl siloxane or "PDMS"), or a derivative thereof. In another embodiment, the silicone is chosen from an aminofunctional silicone, amino-polyether silicone, alkyloxylated silicone, cationic silicone, ethoxylated silicone, propoxylated silicone, ethoxylated/propoxylated silicone, quaternary silicone, or combinations thereof.

In one embodiment, the benefit agent is an enzyme. Suitable enzymes include proteases, amylases, cellulases, lipases, xylogucanases, pectate lyases, mannanases, bleaching enzymes, cutinases, and mixtures thereof.

In one embodiment, the benefit agent comprises an aversive material such as a bitterant material or a pungent material to deter or prevent ingestion of an article incorporating the aversive material, e.g. by a child or animal. The bitterant adds a bitter taste to the composition to which it is added. Suitable bitterants include denatonium salts (e.g., denatonium benzoate, denatonium saccharide, denatonium chloride), sucrose octaacetate, quinine, flavonoids (e.g., quercetin, naringen), and quassinoids (e.g., quassin, brucine). The pungent adds a sharp biting taste when ingested and a burning sensation when topically applied to the skin. Suitable pungents include capsaicin, piperine, allyl isothiocyanate, and resinferatoxin. Suitable levels of incorporation vary according to the particular bitterant or pungent material. As understood by the skilled artisan, the aversive component should be incorporated as a level sufficiently high to impart the unpleasant taste or sensation, yet sufficiently low to avoid potential toxicity from the aversive itself. Denatonium benzoate is particularly suitable in this regard, as its bitterness threshold is substantially lower than its toxicity threshold.

In one embodiment, the benefit agent is an oral care active. Suitable oral care actives include prevention agents including, but not limited to: sodium fluoride, stannous fluoride, sodium monofluorophosphate; dentinal hypersensitivity treatments including, but not limited to: potassium nitrate, strontium chloride and stannous fluoride; gingivitis prevention and treatment agents, including, but not limited to stannous fluoride, triclosan, cetyl pyridinium chloride and chlorhexidine; dental erosion prevention agents including, but not limited to: sodium fluoride, stannous fluoride and sodium polyphosphate; periodontitis treatment agents including, but not limited to chlorhexidine, tetracycline, doxycycline, and ketoprofen; dry mouth amelioration agents including, but not limited to pilocarpine, pellitorin.

In one embodiment, the benefit agent is a personal health care active. Suitable personal health care actives include Personal Healthe care: Cold and flu treatments including, but not limited to, Anti histamines, such as diphenhydramine hydrochloride, Doxylamine succinat, Chlorpheneramine Maleate, fexofenadine, terfenadine, cetirizine Decongestants; such as Phehylephrine Hydrochloride, Pseudoephedrine, Oxymetazoline, Expectorants, such as Guiafenesin, Cough Suppressants; such as dextromethorpand hydrobromide, Antipyretics and Analgesics, such as Acetaminophen, Ibuprofen, Naproxen, Aspirin. Antacids including but not limited to Acid reducers such as, magnesium Hydroxide, Alumimum Hydroxide, Calcium carbonate, Sodium bicarbonate, simethicone; H2 Antagonist, such as, cimetidine, ranitidine, famotidine; Proton Pump inhibitors, such as Omeprazole, Pantoprazole. Antidiarrheals including but not limited to bismuth subsalicylate, loperamide. Probiotics including but not limited to *Bifidobacterium infantis, Lactobacillus acidophilus*. Bulk forming fibers including but not limited to Psyllium.

The mat of the material may be formed by a single strand coming from a single nozzle or from multiple strands, each produced by its own nozzle. If multiple strands are deployed, different strands can be made from different materials and some of these materials may be normally incompatible with one another, for example a detergent and a bleach. In the final product, the strands are physically separated in space, except for the few points where strands touch one another. Because these strands are so separated, otherwise incompatible materials can coexist within the same product without negatively impacting one another. The same is true when the mat is formed by feeding a single strand from a single nozzle when the nozzle feeds different materials at different times.

The strand(s) may be formed into a mat of the material by overlapping the strand(s) during deposition upon a target surface, or by air or hydroentangling the strands, or by other means known for the production of nonwoven materials from strands. The target surface may be heated to maintain the disposed strands of material at or above the phase transition temperature and maintain the material as a semi solid. In an embodiment, wherein the material is allowed to cool to a solid state, the material may be reheated using a heated surface or by irradiating the material using infra-red or other electromagnetic radiation.

While the material is in a semi-solid state and supported by either the original target surface used for the deposition of the strand, or a subsequent support surface, pressure may be applied to the material such that the strand portions comprising the external surface of the material may be compressed and that portion of the material may be locally densified. This may be done to only a portion of the exterior surface of the mat of material or may be done to the entire external surface of the mat of material to locally densify the entire external surface and form an exterior shell rendering the mat as a shell-core structure comprised of the deposited strands. In this manner, the result is an article unfirmly comprised of the deposited strands while having a shell-core structure wherein the shell differs form the core by having a greater density than the core of the article.

In one embodiment, a large mat of the material may be formed from the strands, in an intermediate step, the large mat may be segmented into discrete portions, each discrete portion may subsequently have a portion of the exterior surface locally densified resulting in the article with a shell-core structure. The formation of the shell-core structure with a density gradient between the shell and core and the formation of discrete articles from the original large mat may be accomplished in a single step wherein the mat is both severed into discrete portions and the discrete portions are subjected to forces which locally densify the external surfaces.

The formation of the articles may be accomplished in a batched manner wherein a predetermined mat portion is disposed upon an anvil and forming unit is then brought into contact with the disposed mat such that the mat is concurrently severed into portions and compressed to form the locally densified surface portions due to the configuration of the forming unit to comprise a contact profile having cutting portions and densifying portions. The cutting portions of the forming unit profile may be configured such that there is zero clearance between the cutting portions and the anvil when the forming unit is moved to the cutting, forming position, or a burst clearance wherein the mat is severed into discrete portions due to insufficient clearance between the anvil and forming unit without the need for actual contact between the anvil and forming unit due the bursting of the strands in the small gap.

The formation of the articles may be accomplished in a continuous fashion wherein the mat is formed continuously by the deposition of strands from one or more nozzles upon a moving target surface which carries the deposited strands away from the nozzle and toward a forming element. In this embodiment, the forming element may comprise a rotating cylinder wherein the cutting and forming profile is disposed upon the circumference of the cylinder and the cylinder is disposed transverse to the moving target surface and disposed such that there is either zero gap between the cutting portion of the profile and the target surface or such that there is a sufficiently small gap between the forming unit and the target surface that the formed mat is severed into discrete elements when passing through the gap due to insufficient clearance for the strands in the gap.

As the units are formed, individual portion of the strands may become fused to each other due to the semi-solid nature of the strand. After the strands are cured the portions may remain fused together.

In one embodiment, continuous formation of the units may comprise passing the formed mat between a matched pair of forming unit rollers. The combination of rollers comprising matched forming unit profiles in the roller circumferences such that the mat passing through the gap between the rollers is separated into individual unit dose portions and the surfaces of the unit dose portions are locally densified. In this embodiment, the mat may be shaped on each of an upper and lower mat surface. The division of the mat into unit does portions and the local densification of the unit dose portion surfaces may occur by passing the mat between a single pair of matched forming unit rollers or by a sequence wherein the mat is passed between a first set of rollers wherein one of the two operations occurs followed by passage of the partially formed mat through a second set of rollers for the remaining forming operation In each formation embodiment, the forming units may impart indicia to the formed units by embossing or debossing the surfaces of the mat during formation. In each embodiment, the shape of the formed units may be configured as an indicia, geometric shape, brand log, trademarked name or other recognizable shape.

In each embodiment, the forming gap may be configured such that the unit dose elements are not completely separated in all instances. In these embodiment, the process may yield multi-dose items comprised of separable unit dose items. The unit dose items joined together in a separable fashion to form the multi-dose item. The multi-dose item including perforated or otherwise frangible divisions between the individual unit dose portions allowing a user to easily separate the individual unit dose portions from the multi-dose item. In these embodiments, the separating portions of the forming profiles of the forming units may be configured to create perforated divisions between unit dose portions or to thin the original mat between unit dose portions to facilitate the separation of the unit dose portions from the multi-dose portion by a user.

After the discrete units have been formed and the external surface portions have been locally densified, the semi-solid strand material may be cured to a fully solid state to prevent subsequent distortion of the shape of the units. The curing may be accomplished actively by cooling the units with a fluid such as air or water, or the curing may be accomplished by maintaining the finished units in an environment below the phase transition temperature of the material of the strands. For some materials, the curing may be achieved by exposing the uncured material to appropriate electromagnetic radiation, such as thermoplastic resins which may be cured using ultra-violet radiation.

EXAMPLES

In non-limiting examples, 3D articles of the present invention are made from extruding 3D Article-Forming Compositions. Article-Forming Compositions are prepared gravimetrically at ambient temperature by combining all ingredients of a 3D Article-Forming Composition (active agents, auxiliary ingredients, if any, and optional ingredients, if any) in a glass jar. The jars are then placed in an oven at 80 C until the ingredients have melted and then the 3D Article-Forming Compositions are stirred/mixed by hand to ensure that the ingredients are sufficiently blended together, for example homogeneously blended. The 3D Article-Forming Compositions are then ready for making into 3D Articles according to the present invention.

TABLE 1

| 3D Article-Forming Composition | Meltable Material | Wt. % of Meltable Material | Particle/Filler | Wt. % of Filler | Benefit Agent | Wt. % of Benefit Agent |
|---|---|---|---|---|---|---|
| F1 | Quaternary Ammonium Compound | 58% | Clay | 8% | Perfume | 3% |
|  | Fatty Acid | 29% | — | — | Perfume Microcapsule | 2% |

The 3D Article-Forming Compositions of Table 1 above are added to an extrusion system. The 3D Article-Forming Compositions are kept at a temperature of 55° C. and are pressurized to 200 PSI and extruded through a 0.7 mm diameter nozzle onto a build platform arranged at 40-inch distance away from the nozzle. Ambient temperature flow of cooling air is directed to the tip of the nozzle. The flow of cooling air is created by two opposite 9 inch×0.002-inch air knifes with an inlet air pressure 10 psi. The build platform is moved randomly during extrusion until about a 1 inch thick layer of randomly patterned 3D mat is built on the build platform. A semi-spherical metal mold is then pressed onto the randomly patterned 3D mat while the 3D mat is still warm to form mini-dome 3D Articles having locally densified external surface portions. The mini-dome 3D Articles are then removed from the build platform once fully cooled.

Particle Size Distribution Method

The particle size distribution may be determined using a laser scattering particle size distribution analyzer. The Cilas, model 1180, available from CILAS, Orleans, France, is an exemplary laser scattering particle size distribution analyzer. In this method, the principle of Fraunhofer scattering theory is used to calculate the size and distribution of particles. Results are displayed on a volume basis. The application of this method was applied to D-Mannitol using Dry mode while applying 500 mb of pressure to disperse the powder in order to get discrete particle sizes. For D-Mannitol sample the results from this particle size analysis are as follows: D10=19 microns, D50=87 microns, D90=235 microns, Mean diameter=107 microns.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming an object, the method comprising: providing semi-solid strands of a meltable material having a diameter of between about 0.5 and about 2 millimeters; embedding from about 0.00001 to about 0.2 millimeter particles in the meltable material to form strands of meltable material comprising particles; forming a non-woven mat comprising the strands of meltable material wherein the strand contains a filler particle comprising a D50 from between about 0.1 microns and about 200 microns; forming discrete units of the non-woven mat into a shape; applying a compressive force to a portion of the discrete units' surface to locally densify that portion of the surface of the discrete units, so that the discrete units have a shell-core structure with a density gradient between the shell and the core, wherein the shell differs from the core by having a greater density than the core of the article; and curing the discrete units of the non-woven mat by cooling.

2. The method according to claim 1, wherein the discrete units further comprise an indicia formed by embossing or debossing.

3. The method according to claim 1, wherein the particles comprise: starches, gums, polysaccharides, proteins, amino acids, water soluble polymers, water degradable polymers, water insoluble polymers, sugars, sugar alcohols, inorganic particles, organic salts, surfactants, fatty amphiphiles and mixtures thereof.

4. The method according to claim 1, wherein the semi-solid meltable strand comprise a material selected from the group consisting of: metals, hydrocarbon based meltable resins, polyethylene, polypropylene, polyethylene glycol, waxes, surfactants, fatty acids, fatty alcohols, fatty esters, fats, starches and chocolate, and combinations thereof.

5. The method according to claim 1, wherein the meltable material is water soluble.

6. The method according to claim 1, wherein portions of the strands are fused to each other.

7. The method according to claim 1, wherein the strands comprise at least one benefit agent.

8. The method according to claim 7, wherein at least one benefit agent is encapsulated in a polymeric shell.

9. The method according to claim 7, wherein the benefit agent is selected from the group consisting of: perfumes, pro-perfumes, builders, heavy metal ion sequestrants, surfactants, fabric softeners, antistatic agents, colorants, pigments, aversive agents, bittering agents, enzymes, coenzymes, enzyme stabilizers, plant derivatives, plant extracts, botanicals, botanical extracts, anti-dandruff agents, anti-foaming agents, oral care actives, personal health care actives, vitamins, anti-bacterial agents, anti-microbial agents, antifungal agents, their derivatives, and mixtures thereof.

10. The method according to claim 7, wherein the strands contain at least one aversive agent and at least one benefit agent selected from the group consisting of: perfume oil, encapsulated perfume oil, builder, surfactant, fabric softener and silicone oil.

11. The method according to claim 7, wherein the strand contains: a benefit agent selected from the group consisting of perfume oil, encapsulated perfume oil, builder, surfactant, fabric softener and silicone oil; and a safe and effective amount of an aversive agent.

12. The method according to claim 11, wherein the D50 is from between about 0.2 to about 150 microns.

13. The method according to claim 12, wherein the D50 is from between about 0.5 and about 100 microns.

* * * * *